US009052282B2

(12) United States Patent
Kussmann et al.

(10) Patent No.: US 9,052,282 B2
(45) Date of Patent: Jun. 9, 2015

(54) WATER ANALYSIS MEASUREMENT ARRANGEMENT

(75) Inventors: Michael Kussmann, Duesseldorf (DE); Lothar Heidemanns, Korschenbroich (DE); Andreas Jonak, Meerbusch (DE); Markus Hahn, Kempen (DE); Heinz Rudde, Hueckelhoven (DE); Claudia Rieger, Duesseldorf (DE); Axel Leyer, Moenchengladbach (DE)

(73) Assignee: HACH LANGE GMBH, Berlin (DE)

( * ) Notice: Subject to any disclaimer, the term of this patent is extended or adjusted under 35 U.S.C. 154(b) by 270 days.

(21) Appl. No.: 13/393,834

(22) PCT Filed: Aug. 5, 2010

(86) PCT No.: PCT/EP2010/061425
§ 371 (c)(1),
(2), (4) Date: Apr. 20, 2012

(87) PCT Pub. No.: WO2011/026707
PCT Pub. Date: Mar. 10, 2011

(65) Prior Publication Data
US 2012/0212234 A1    Aug. 23, 2012

(30) Foreign Application Priority Data
Sep. 3, 2009    (EP) .................................... 09169372

(51) Int. Cl.
*G01N 27/416*    (2006.01)

(52) U.S. Cl.
CPC ........ *G01N 27/4163* (2013.01); *G01N 27/4167* (2013.01)

(58) Field of Classification Search
CPC ... G01N 27/30; G01N 27/301; G01N 27/403; G01N 27/28; G01N 27/333; G01N 27/413; G01N 27/416; G01N 27/4163; G01N 27/4165; G01N 27/4167

USPC .......... 324/425–450; 204/416–420, 433, 435; 205/787.5, 789, 743; 422/68.1, 422/82.01–82.04
See application file for complete search history.

(56) References Cited

U.S. PATENT DOCUMENTS 3,661,748 A * 5/1972 Blackmer ...................... 204/401
4,189,367 A * 2/1980 Connery et al. ........... 205/787.5
(Continued)

FOREIGN PATENT DOCUMENTS

DE    19539763 A1 * 4/1997 ............. G01N 27/30
DE    196 26 277 A1    1/1998
(Continued)

OTHER PUBLICATIONS

G. S. Popkirov et al.: "A New Impedance Spectrometer for the Investigation of Electrochemical Systems", Review of Scientific Instruments, vol. 63, No. 11, pp. 5366-5372 (Nov. 1992).

*Primary Examiner* — Huy Q Phan
*Assistant Examiner* — James Split
(74) *Attorney, Agent, or Firm* — Norman B. Thot

(57) ABSTRACT

A water analysis measurement arrangement for determining a concentration of ions and/or ionic compounds in an aqueous medium includes a closed buffer solution housing comprising a pH buffer solution. The closed buffer solution housing is configured to communicate with the aqueous medium via an electrolyte bridge. A reference electrode is arranged in the closed buffer solution housing. An amplifier ground is disposed on a ground electrode and is configured to directly contact the aqueous medium. A high-impedance amplifier comprises a first capacitive element arranged between the reference electrode and the amplifier ground. An AC voltage generator is arranged between the amplifier ground and the ground electrode. A measurement electrode is configured to directly contact the aqueous medium. A redundant unit comprises a separate low-impedance redundant electrode arranged in the closed buffer solution housing and a high-impedance redundant electrode amplifier comprising a second capacitive element to the amplifier ground.

14 Claims, 1 Drawing Sheet

(56) References Cited

U.S. PATENT DOCUMENTS

| | | | |
|---|---|---|---|
| 4,401,548 A * | 8/1983 | Brezinski | 204/435 |
| 4,461,998 A | 7/1984 | Kater | |
| 4,686,011 A * | 8/1987 | Jackle | 205/787.5 |
| 4,777,444 A * | 10/1988 | Beijk et al. | 324/439 |
| 4,822,456 A * | 4/1989 | Bryan | 205/789 |
| 6,395,158 B1 | 5/2002 | King et al. | |
| 6,685,807 B2 * | 2/2004 | Meier | 204/401 |
| 6,856,930 B2 * | 2/2005 | Ammann | 702/116 |
| 6,894,502 B2 * | 5/2005 | Feng et al. | 324/438 |
| 7,511,504 B2 * | 3/2009 | Pechstein et al. | 324/438 |
| 2010/0140088 A1 * | 6/2010 | Yeon et al. | 204/406 |

FOREIGN PATENT DOCUMENTS

| | | |
|---|---|---|
| EP | 0 156 376 A2 | 10/1985 |
| EP | 1 219 959 A1 | 7/2002 |
| GB | 2 036 977 A | 7/1980 |
| WO | WO 2007 023031 A1 | 3/2007 |

* cited by examiner

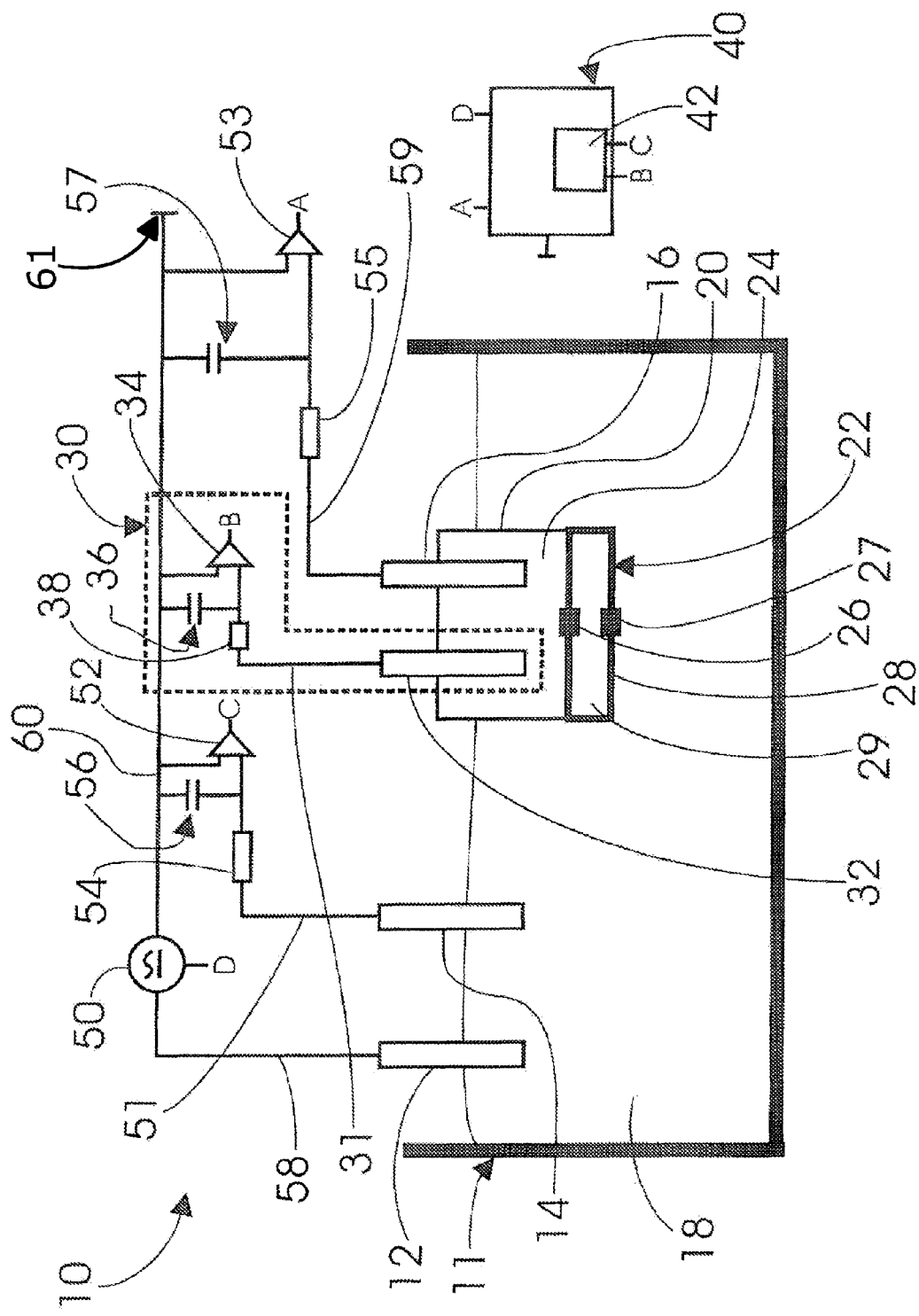

WATER ANALYSIS MEASUREMENT ARRANGEMENT

CROSS REFERENCE TO PRIOR APPLICATIONS

This application is a U.S. National Phase application under 35 U.S.C. §371 of International Application No. PCT/EP2010/061425, filed on Aug. 5, 2010 and which claims benefit to European Patent Application No. 09169372.1, filed on Sep. 3, 2009. The International Application was published in German on Mar. 10, 2011 as WO 2011/026707 A1 under PCT Article 21(2).

FIELD

The present invention provides a water analysis measurement arrangement for determining ions and/or ionic compounds in an aqueous medium.

BACKGROUND

A water analysis measurement arrangement for determining ions or ionic compounds solvated in water, in particular for determining the concentration of hydrogen ions, i.e., the so-called pH, is known from the prior art. Such systems, e.g., for determining pH, function according to the principle of electrochemical cells that are typically designed as glass electrodes or so-called combination electrodes.

A conventional electrochemical cell comprises two separate half-elements that each accommodate an electrode, one of the half-elements containing a measuring electrode and the other half-element containing a reference electrode. Both half-elements are in separate solutions which are connected through an electrolyte bridge. As an alternative, both half-elements may also be immersed in a common solution. The two half-elements together form a measuring chain.

Regarding the structure, an electrochemical cell of this type is often realized as a double-walled glass tube. The inner tube contains a measuring electrode. The inner tube also has a semi-permeable glass membrane at the end thereof which establishes the contact to the measurement solution. The outer tube accommodates a reference electrode in contact with the measurement solution through an electrolyte bridge, such as a double diaphragm or a single diaphragm. Both tubes are usually filled with a neutral buffered electrolyte solution with a pH of 7.

What is measured is the electrical voltage between the reference electrode and the measurement electrode which itself depends on the hydrogen ion concentration in the measurement solution.

This design of a combination electrode has a weak point in the diaphragm that establishes an electric contact between the reference electrode and the measurement solution. Depending on the concentration of the ions present in the measurement solution, different chemical potentials between the reference electrode chamber and the measurement electrode may gradually cause a contamination and/or a dilution of the buffered electrolyte solution in the reference electrode chamber. Such a contamination and/or dilution have the effect that the pH indicated does not reflect the actual hydrogen ion concentration. If the contamination and/or dilution is too marked, the existing electrolyte solution must also be replaced which requires substantial effort. A soiling and/or contamination of the diaphragm facing the measurement solution may also occur, thereby resulting in significant erroneous potentials.

When used in an industrial control process, such a design has a further problem, that being the electrical noise of the environment in which the pH system is installed. This results in measurement inaccuracies that may have serious consequences in an industrial control process.

A water analysis measurement arrangement described in US 6 395 158 B1 solves the problem of electrical noise. A third electrode, the so-called ground rod, is here provided in addition to the known dual-electrode arrangement, wherein a measurement of the differential between the measurement electrode and the reference electrode is performed with respect to the third electrode, i.e., the ground rod.

A water analysis measurement arrangement is described in WO 2007 023031 A1 which overcomes the weakness of the electrolyte bridge. The individual diaphragm is here replaced with a chamber including two individual diaphragms, the chamber being filled with an electrolyte. Due to this arrangement, the electrolyte solution in the reference electrode chamber can no longer be contaminated or diluted to the extent found in conventional arrangements. However, it is not possible to provide perfect protection of the electrolyte bridge in an attempt to avoid contamination or dilution, since the electrolyte bridge would then lose the necessary permeability. The condition of the electrolyte bridge has a significant influence on the reference signal quality so that this represents a source of errors that may have adverse effects on a control process.

SUMMARY

An aspect of the present invention is to provide a water analysis measurement arrangement with improved reliability.

In an embodiment, the present invention provides a water analysis measurement arrangement for determining a concentration of at least one of ions and ionic compounds in an aqueous medium which includes a closed buffer solution housing comprising a pH buffer solution. The closed buffer solution housing is configured to communicate with the aqueous medium via an electrolyte bridge. A reference electrode is arranged in the closed buffer solution housing. An amplifier ground is disposed on a ground electrode and is configured to directly contact the aqueous medium. A high-impedance amplifier comprises a first capacitive element arranged between the reference electrode and the amplifier ground. An AC voltage generator is arranged between the amplifier ground and the ground electrode. A measurement electrode is configured to directly contact the aqueous medium. A redundant unit comprises a separate low-impedance redundant electrode arranged in the closed buffer solution housing and a high-impedance redundant electrode amplifier comprising a second capacitive element to the amplifier ground.

BRIEF DESCRIPTION OF THE DRAWINGS

The present invention is described in greater detail below on the basis of embodiments and of the drawing in which:

FIG. 1 shows a schematic illustration of the water analysis measurement arrangement of the present invention.

DETAILED DESCRIPTION

The water analysis measurement arrangement of the present invention comprises a closed buffer solution housing holding a pH buffer solution, the housing being in communication with an aqueous medium through an electrolyte bridge, whose concentration of ions and/or ionic compounds in an aqueous medium is to be determined. The high-impedance reference electrode arranged in the buffer solution housing is connected to a high-impedance amplifier, a capacitive element being connected between the reference electrode and the amplifier ground. The amplifier ground is provided on a ground electrode that is in direct contact with the aqueous medium. The water analysis measurement arrangement further comprises a measurement electrode in direct contact with the aqueous medium, and an AC voltage generator provided between the amplifier ground and the ground electrode. The water analysis measurement arrangement further comprises a redundant unit that includes a separate low-impedance redundant electrode in the pH buffer solution in the closed buffer solution housing and a high-impedance redundant electrode amplifier with a capacitive element to the amplifier ground.

Such a water analysis measurement arrangement comprising a redundant unit allows for a complete impedance monitoring of the electrolyte bridge and provides a second, additional reference potential that is obtained by introducing an additional second electrode, namely, the redundant electrode, into the buffer solution housing and by a corresponding wiring and evaluation. The additional second electrode is a very low-impedance electrode. A series connection of the low-impedance electrolyte bridge and the additional rather low-impedance redundant electrode thus allows the impedance of the electrolyte bridge through a suitable amplifier to be determined. The amplifier of the redundant electrode and of the reference electrode should have a respective internal resistance that is higher by at least a factor of 100 to 1,000 than the inner resistance of the reference electrode and the redundant electrode, respectively, so that the useful signal can be amplified and evaluated accordingly.

In an embodiment of the present invention, the water analysis measurement arrangement can, for example, comprise a depletion detector connected to the redundant electrode amplifier, the detector outputting a signal when the internal resistance of the electrolyte bridge reaches a limit value, i.e., exceeds the value or falls below the same. A user can thus be informed in time about a critical state of the measurement arrangement so that precautions can be taken to guarantee a constant quality of the measurements and to avoid unnoticed erroneous measurements.

In an embodiment of the present invention, the water analysis measurement arrangement can, for example, comprise a redundant electrode with an internal resistance that is lower by at least a factor of 100 than the internal resistance of the reference electrode. Given a corresponding series connection of the low-impedance redundant electrode and the low-impedance electrolyte bridge, a monitoring of the electrolyte bridge thus can be ensured. Such a monitoring is not possible with a high-impedance pH electrode, since slight variations of the electrolyte bridge impedance cannot be reliably detected thereby.

In an embodiment of the present invention, the water analysis measurement arrangement can, for example, comprise an electrolyte bridge with an internal resistance that is higher by at most a factor of 100, for example, by at most a factor of 10, than the internal resistance of the redundant electrode. It can thus be ensured that even slight variations of the electrolyte bridge impedance can be detected.

The water analysis measurement arrangement can, for example, comprise an electrolyte bridge formed by a separate electrolyte chamber equipped with two diaphragms and including an electrolyte solution or an electrolyte gel. The two diaphragms are arranged such that one diaphragm forms a connection between the electrolyte and the pH buffer solution and the other diaphragm forms a connection between the electrolyte and the aqueous medium. With this structure, the pH shift caused by a contamination and/or a dilution of the electrolyte is smaller by at least a factor of 40 and thereby a more accurate analysis of the aqueous medium can be obtained than with an electrolyte bridge formed by a single diaphragm where all of the contamination acts directly on the buffer solution.

In an embodiment of the present invention, the water analysis measurement arrangement can, for example, include a pH buffer solution which is a neutral pH solution, wherein salts are used to adjust the neutral pH solution to an appropriate molarity. The neutral pH solution can, for example, be formed by salts of at least one of potassium chloride, potassium nitrate and sodium chloride, and the neutral pH solution can, for example, be buffered with an acid-base buffer.

In an embodiment of the present invention, the water analysis measurement arrangement comprises a buffer solution housing containing a minimum volume of a pH buffer solution of 3 to 5 ml. Since the electrolyte will be contaminated and/or diluted over time, the use of a larger buffer solution housing filled with a correspondingly large volume of a pH buffer solution makes it possible to prolong the lifetime of such a measurement arrangement.

The water analysis measurement arrangement can, for example, be designed for use in determining ions and/or ionic compounds. The ions are formed by the elements hydrogen, chlorine, sodium and/or potassium. The ionic compounds are typically formed by compounds of sulphur, nitrogen and/or phosphor.

In an embodiment of the present invention, the redundant electrode can, for example, be a metal electrode of particularly low impedance. In a series connection between the low-impedance redundant metal electrode and the low-impedance electrolyte bridge, the impedance and thus the quality of the electrolyte bridge can be controlled in a reliable and continuous manner.

In an embodiment of the present invention, the reference electrode can, for example, be in the form of a glass electrode, a platinum electrode, a silver chloride electrode or a calomel electrode. A glass electrode is less susceptible to foreign ions that can enter the buffer solution housing as a result of contamination, irreversibly adhere to the electrodes and corrupt the signal.

In an embodiment of the present invention, the ground electrode can, for example, be made of an electrically conductive material such as steel, platinum or titanium or, for example, of a conductive plastic material.

The water analysis measurement arrangement can, for example, comprise a measurement electrode which may be an ion-selective electrode or a pH electrode.

FIG. 1 schematically illustrates a water analysis measurement arrangement 10 for the determination of ions and/or ionic compounds in an aqueous medium 18, which aqueous medium 18 is contained in a basin 11. Arranged in the basin 11 is a buffer solution housing 20 which is a part of the measuring arrangement and comprises a redundant unit 30, a reference electrode 16 and an electrolyte bridge 22.

The redundant unit 30 is formed by a redundant electrode 32, a series resistor 38, a capacitive element 36 and an amplifier 34, the amplifier 34 comprising a signal output B which signal output B is connected to a depletion detector 42 that is a part of a central unit 40. The redundant electrode 32 is connected to the amplifier 34 by means of a signal line 31 and via the series resistor 38, the amplifier 34 referring to a ground line 60. A capacitive element 36 is further arranged between the series resistor 38 and the amplifier 34, the capacitive element 36 being connected to the ground line 60.

The amplifiers typically used herein are high-impedance operational amplifiers with a gain of one, having an inverting input connected to the ground line 60 and a non-inverting input connected to the useful signal to be amplified.

The buffer solution housing 20 is filled with a pH buffer solution 24. The reference electrode 16 and the redundant electrode 32 are immersed in the pH buffer solution 24 and are in direct contact with the pH buffer solution 24.

The electrolyte bridge 22 is formed by a separate electrolyte chamber 28 filled with an electrolyte 29 and by two diaphragms 26, 27 arranged such that the one diaphragm 26 establishes communication from the electrolyte 29 to the pH buffer solution 24 and the second diaphragm 27 establishes communication from the electrolyte 29 to the aqueous medium 18.

A measurement electrode 14 and a ground electrode 12 are further arranged in the basin 11 as a part of the measurement arrangement 10, both being in direct contact with the aqueous medium 18. A ground electrode line 58 connects the ground electrode 12 to an AC voltage generator 50, which AC voltage generator 50 is connected to the central unit 40 via a control input D. The AC voltage generator 50 is further connected to the ground line 60. The amplifier ground 61 is provided on the ground electrode 12 that is in direct contact with the aqueous medium 18.

The measurement electrode 14 is connected to an amplifier 52 by means of a signal line 51 and via a series resistor 54, the amplifier 52 having a signal output C, which signal output C is connected to a depletion detector 42. The amplifier 52 is also connected to the ground line 60. A capacitive element 56 is further arranged between the series resistor 54 and the amplifier 52, the capacitive element 56 being connected to the ground line 60.

The reference electrode 16 is connected to an amplifier 53 through a signal line 59 and via a series resistor 55, the amplifier 53 having a signal output A, which signal output A is connected to the central unit 40. The amplifier 53 is further connected to the ground line 60. A capacitive element 57 is also arranged between the series resistor 55 and the amplifier 53, the capacitive element 57 being connected to the ground line 60.

The impedance measurement of the electrolyte bridge 22 is effected via the redundant electrode 32, the redundant electrode 32 being connected to the signal input of the amplifier 34. The redundant electrode 32 generates a DC voltage signal proportional to the logarithm of the redox potential of the pH buffer solution 24. Since the pH buffer solution 24 is in contact with the aqueous medium 18 through the electrolyte bridge 22, a stable reference potential is generated. The reference electrode 16 immersed in the pH buffer solution 24 also generates such a reference potential.

For an impedance determination of the electrolyte bridge 22, the AC voltage generator 50 outputs a low-frequency alternating signal into the aqueous medium 18 via the ground electrode 12, whereby said signal is applied to the entire measurement arrangement 10. The capacitive element 36 at the signal input of the redundant electrode amplifier 34 generates an AC voltage inversely proportional to the impedance of the redundant electrode 32. The same is amplified by the amplifier 34, and the output signal is supplied to the depletion detector 42. The output signal is there digitized by means of an A/D conversion and is compared to a limit value. If the limit value is reached, a depletion signal is outputted. In this manner, the impedance of the electrolyte bridge 22 is determined and evaluated so that the electrolyte bridge 22 or the water analysis measurement arrangement 10 can be replaced in time before it causes erroneous measurements.

The redundant electrode 32 can also be used as a reference system or as a control system for the reference electrode 16.

The present invention is not limited to embodiments described herein; reference should be had to the appended claims.

What is claimed is:

1. A water analysis measurement arrangement for determining a concentration of at least one of ions and ionic compounds in an aqueous medium, the water analysis measurement arrangement comprising:
    a closed buffer solution housing comprising a pH buffer solution, the closed buffer solution housing being configured to communicate with the aqueous medium via an electrolyte bridge;
    a reference electrode arranged directly in the closed buffer solution housing so as to have a direct electrical contact with the pH buffer solution;
    an amplifier ground;
    a ground electrode configured to directly contact the aqueous medium;
    a high-impedance amplifier comprising a first capacitive element arranged between the reference electrode and the amplifier ground to which the first capacitive element is directly connected;
    an AC voltage generator arranged between the amplifier ground and the ground electrode, the AC voltage generator being configured to output a low-frequency alternating signal;
    a measurement electrode configured to directly contact the aqueous medium and being connected to an amplifier which is connected to the amplifier ground; and
    a redundant unit comprising a separate low-impedance redundant electrode arranged directly in the closed buffer solution housing so as to have a direct electrical contact with the pH buffer solution, the separate low-impedance redundant electrode being connected to a high-impedance redundant electrode amplifier comprising a second capacitive element being directly connected to the amplifier ground,
    wherein,
    the amplifier ground is electrically disposed on the ground electrode if the AC voltage generator does not output the low-frequency alternating signal, and the low frequency alternating signal is induced into the aqueous medium via the ground electrode so as to allow an impedance determination of the electrolyte bridge, if the AC voltage generator outputs the low-frequency alternating signal, and
    the electrolyte bridge comprises an electrolyte chamber and an electrolyte solution or an electrolyte gel, wherein the electrolyte chamber comprises a first diaphragm and a second diaphragm.

2. The water analysis measurement arrangement as recited in claim 1, wherein an internal resistance of the low-impedance redundant electrode is at least 100 times lower than an internal resistance of the reference electrode.

3. The water analysis measurement arrangement as recited in claim 1, further comprising an electrolyte bridge depletion detector, wherein the electrolyte bridge depletion detector is connected to the high-impedance redundant electrode amplifier and is configured to output a depletion signal when an internal resistance of the electrolyte bridge reaches a limit value.

4. The water analysis measurement arrangement as recited in claim 3, wherein the internal resistance of the electrolyte bridge is up to 100 times higher than an internal resistance of the low-impedance redundant electrode.

5. The water analysis measurement arrangement as recited in claim 3, wherein the internal resistance of the electrolyte bridge is up to 10 times higher than an internal resistance of the low-impedance redundant electrode.

6. The water analysis measurement arrangement as recited in claim 1, wherein the pH buffer solution comprises a neutral pH solution.

7. The water analysis measurement arrangement as recited in claim 6, wherein the neutral pH solution is formed by salts of at least one of potassium chloride, potassium nitrate and sodium chloride, and the neutral pH solution is buffered with an acid-base buffer.

8. The water analysis measurement arrangement as recited in claim 1, wherein the closed buffer solution housing comprises a volume of at least 3 to 5 ml of the pH buffer solution.

9. The water analysis measurement arrangement as recited in claim 1, wherein the at least one of ions and ionic compounds are hydrogen, chloride, sodium, potassium, sulfate, ammonium, phosphate and nitrate.

10. The water analysis measurement arrangement as recited in claim 1, wherein the separate low-impedance redundant electrode is a metal electrode.

11. The water analysis measurement arrangement as recited in claim 1, wherein the reference electrode is a glass electrode, a platinum electrode, a silver chloride electrode or a calomel electrode.

12. The water analysis measurement arrangement as recited in claim 1, wherein the ground electrode is made of a conductive material.

13. The water analysis measurement arrangement as recited in claim 12, wherein the conductive material is a steel, platinum, titanium or a conductive plastic.

14. The water analysis measurement arrangement as recited in claim 1, wherein the measurement electrode is an ion-selective electrode or a pH electrode.

* * * * *